(12) United States Patent
Weihrauch

(10) Patent No.: US 6,421,867 B1
(45) Date of Patent: Jul. 23, 2002

(54) BRUSH, IN PARTICULAR FOR AN ELECTRIC TOOTHBRUSH

(75) Inventor: Georg Weihrauch, Wald-Michelbach (DE)

(73) Assignee: Coronet-Werke GmbH, Wald-Michelbach (DE)

( * ) Notice: Subject to any disclaimer, the term of this patent is extended or adjusted under 35 U.S.C. 154(b) by 0 days.

(21) Appl. No.: 09/463,850

(22) PCT Filed: Jul. 22, 1998

(86) PCT No.: PCT/EP98/04602

§ 371 (c)(1),
(2), (4) Date: Feb. 1, 2000

(87) PCT Pub. No.: WO99/07251

PCT Pub. Date: Feb. 18, 1999

(30) Foreign Application Priority Data

Aug. 7, 1997 (DE) .......................................... 197 34 287

(51) Int. Cl.[7] .............................................. A46B 13/02
(52) U.S. Cl. ........................................... 15/28; 15/22.1

(58) Field of Search .......................... 15/22.1, 28, 167.1

(56) References Cited

U.S. PATENT DOCUMENTS

| 5,173,983 A | 12/1992 | Le |
| 5,613,262 A | 3/1997 | Choy-Maldonado |

FOREIGN PATENT DOCUMENTS

| DE | 86 06 012.0 | 9/1990 |
| DE | 295 16 571 | 2/1996 |
| EP | 0 651 978 | 5/1995 |
| GB | 108 829 | 9/1917 |

*Primary Examiner*—Randall E. Chin
(74) *Attorney, Agent, or Firm*—Paul Vincent

(57) ABSTRACT

A brush, in particular for an electrical toothbrush, having a brush head driven in at least one direction and bristles attached thereto is distinguished in that the ends of at least one portion of the bristles lie on a strip-like or spotted enveloping surface and at least those border edges of the enveloping surface formed by the bristles leading in the direction of motion of the brush head extend at an angle with respect to the direction of motion of the brush head which is different than 90°.

14 Claims, 2 Drawing Sheets

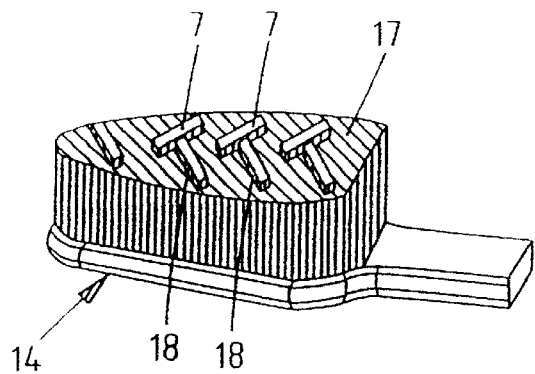
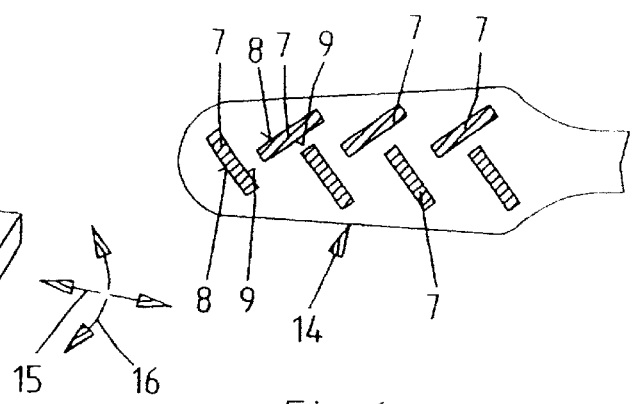
Fig.5　　　　　　　　　Fig.6
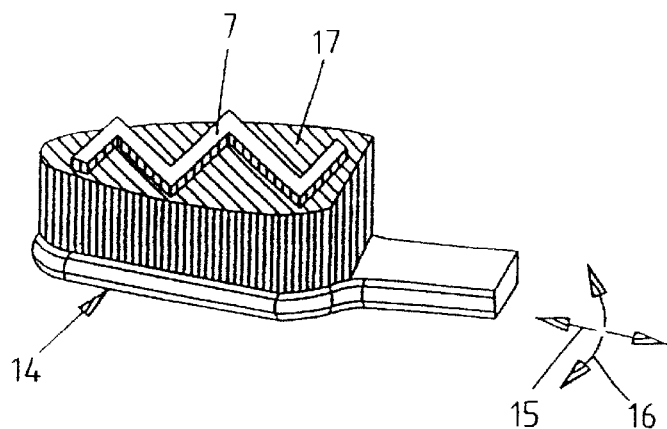
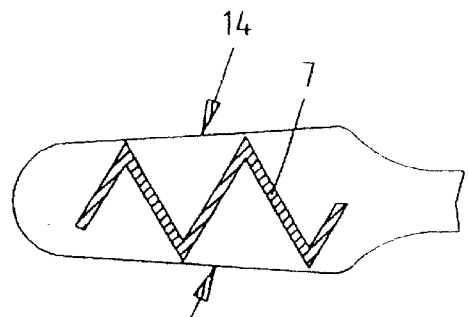
Fig.7　　　　　　　　　Fig.8

BRUSH, IN PARTICULAR FOR AN ELECTRIC TOOTHBRUSH

BACKGROUND OF THE INVESTIGATION

The invention concerns a brush, in particular for an electric toothbrush having a brush head driven in at least one direction with bristles attached thereto.

The invention generally concerns driven brushes, in particular however those of electric toothbrushes.

Substantially two factors are important for the cleaning and massaging effect of a toothbrush on teeth and gums which are independent of whether or not the toothbrush is driven manually or electrically. These are the bristle stock and the motion with which the bristle stock is guided over the teeth and the gums. When cleaning by hand, substantially linear motions are effected along the row of teeth as well as perpendicular thereto (red-white). These are however normally overlapped with other more or less random motion components. In this manner a full area brushing effect is generally guaranteed: the bristles penetrate sufficiently into the spaces between the teeth and also into the fine fissures of the teeth surfaces. This is supported in addition through particular features of the bristle stock, e.g. V-shaped bristle bundles, non-planar shapes, contoured brush surfaces and the like.

With electric toothbrushes which are normally held in a particular position by the user and are guided in a substantially linear fashion, the components of motion, in contrast to the random manual guidance of the hand toothbrush, are limited by the drive mechanism. With elongated brush heads, similar to the hand toothbrushes, a combination of linear (axial) and pivoting motion is conventional. With round brush heads, rotational motion, sometimes superimposed by an upward and downward motion in the direction of the bristles, is preferred. Finally, bristle heads having drives are known in the art with which a few bristle bundles are displaced normally in pairs in rotational oscillation. The more components of motion the more complex the drive and the greater its susceptibility to failure.

The brush head of a conventional electric toothbrush (US 5 173 983) has a soft peripheral edge at which the brush head is supported on the teeth surfaces or on the gums. The bristle stock is mounted in a recessed manner within this soft peripheral edge. The bristles protrude past the peripheral edge. They are disposed in a manner similar to a bucket wheel and extend from the center of rotation of the brush head in an outward direction in three curved strips. The bristles disposed at the center are somewhat longer than the others and join together into a spike for penetrating, in particular, into inter-dental cavities and between the teeth and the edge of the gums. With this conventional brush head, the degree of pressing of the bristles is limited by the seating of the peripheral edge and decreases as the bristles wear. In addition, brushing action is effected only by a fraction of the brush head, since there are no bristles between the curved bristle strips. This leads to a reduction in effectiveness. The brushing direction is limited to the direction of rotation of the brush head. Residual food particles, soiling, and residual toothpaste settle into the recessed region within the soft peripheral edge and near the lower ends of the bristle bundles.

SUMMARY OF THE INVENTION

This purpose is achieved with a driven brush head having bristles attached thereto in that the ends of at least one portion of the bristles protrude beyond the remaining evenly covering bristle-stock and are disposed within a striped or spotted enveloping surface and at least the border edge of the enveloping surface formed by the leading bristles in the direction of motion of the brush head extends at an angle relative to the direction of motion of the brush head which differs from 90°.

The angular position of the border edge of the enveloping surface formed by the protruding bristles relative to the direction of motion of the brush head results in at least one component of motion at an angle with respect to the component of motion given by the drive. If the border edge is not linear, rather has a plurality of angles or is corrugated or has a plurality of enveloping surfaces with different angles relative to the direction of motion of the drive, a plurality of motional directions thereby result with an associated plurality of cleaning and massaging effects. The shorter, evenly covering bristle stock thereby guarantee full surface brushing. The brush head seats at this shorter bristle stock during brushing, wherein the protruding bristles can also penetrate into the inter-dental spaces and beneath the edge of the gums.

The leading and trailing border edges of the enveloping surface formed by the bristles can be substantially parallel so that a strip-shape bristle surface results. The two border edges can also extend at differing angles relative to the direction of motion of the brush head so that spotted brush surfaces result which are particularly effective with an oscillating drive since, in dependence on the direction of motion of the drive, further additional components of motion are overlapped in various directions.

The dependent claims recite various preferred embodiments for a brush head driven to rotate about an axis or oscillate. Among these embodiments, only two are focused upon here. In the event of a spiraling enveloping surface, the rotation or rotational oscillation motion is overlapped with additional circular motion of variable radius. The same is true for an S-shaped configuration of the enveloping surface particularly when a plurality of S-shaped striped enveloping surfaces are provided, similar to the shape of a bucket wheel.

The dependent claims characterize embodiments with an elongated brush head having a linear drive in the direction of the longitudinal axis which, if appropriate, can be overlapped-by an oscillating pivoting motion perpendicular thereto. In particular, zigzagged or arrow shaped striped enveloping surfaces have turned out to be especially effective.

The invention is described below with reference to the embodiment shown in the drawing.

BRIEF DESCRIPTION OF THE DRAWING

FIG. 5 shows a perspective view of a fourth embodiment of a linearly driven brush with optional oscillating motion;

FIG. 6 shows a plan view of the fourth embodiment of FIG. 5;

FIG. 7 shows a perspective view of a fifth embodiment of a linearly driven brush with optional oscillating motion;

FIG. 8 shows a plan view of the fifth embodiment of FIG. 7.

DESCRIPTION OF THE PREFERRED EMBODIMENT

Figure 1:
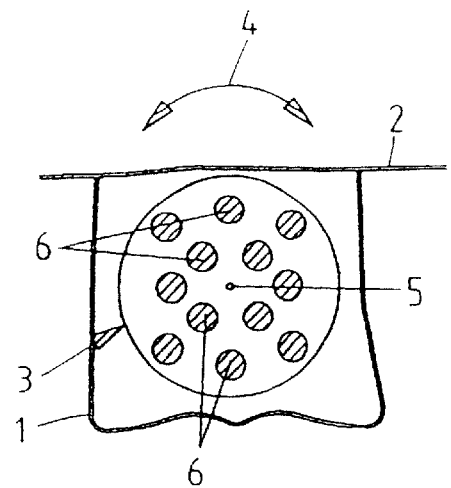
FIG. 1 shows a view of a brush head of an electrical toothbrush having a rotating or ocsillating brush head of conventional construction during operation phase.

FIG. 1 shows a tooth 1, in this case an upper molar, and the gingival border 2. In addition, a circular brush head 3 is shown which is mounted onto the drive of an electrical tooth brush. The brush head is driven in a rotating or oscillating manner, if appropriate, with additional vibrating motion in an axial direction. Motion about the axis 5 is indicated with the double arrow 4.

The embodiment in accordance with FIG. 1 concerns a conventional brush head. It is configured with substantially circular bristle bundles 6. The bundles 6 or the ends of the bristles forming the bundles define a substantially circular enveloping surface. When the brush head is driven, the bundles describe a circular motion about the axis of rotation. Their active surface on the surface of the tooth 1 is limited to short ring-shaped sections by the oscillating rotating motion. Substantial areas of the tooth remain untreated or experience only a processing in association with corresponding intensive manual guiding motions of the electrical toothbrush.

Figure 2:
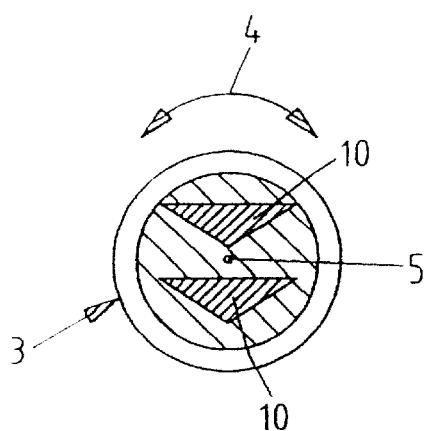
FIG. 2 shows a first embodiment of a brush head having a rotating or oscillating drive.
Figure 3:
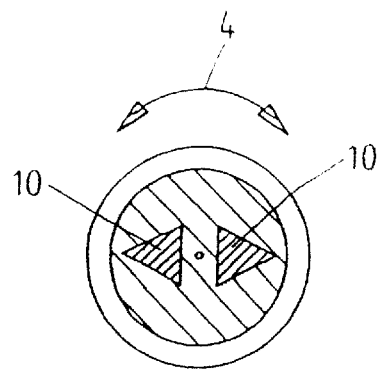
FIG. 3 shows a second embodiment of a brush head having a rotating or oscillating drive.

In the embodiments in accordance with FIGS. 2 and 3, the bristle stock has bristles whose ends lie in spot-like enveloping surfaces 10. In FIG. 2, the enveloping surfaces 10 are configured as triangles pointing in a common direction and are disposed outside the axis of rotation 5. In the embodiment in accordance with FIG. 3, the triangular shaped enveloping surfaces face away from each other. In all cases, the substantive active surfaces of the bristles are disposed at angles relative to the axis of rotation and there are a plurality of such active working surfaces. In both embodiments, the free surfaces of the brush head are configured with bristles 13 or with bundles of shorter length beyond which the bristles in the enveloping surface 10 protrude.

Figure 4:
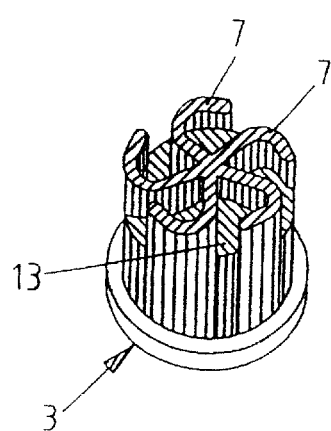
FIG. 4 shows a third embodiment of a brush head having a rotating or oscillating drive.

In the embodiment in accordance with FIG. 4, the ends of the bristles lie on a stripe-shaped enveloping surface 7 having an S-shape, wherein the S-curve has its cusp point in the axis 5 of the brush head 3. In the embodiment shown, a plurality of such S-shaped enveloping surfaces 7 are disposed in a manner of a bucket wheel. In this case as well, there are a plurality of active directions at the leading border edges 8, 9 of the enveloping surface 7. The bristles situated in the enveloping surface 7 are disposed within a full surface bristle stock 13, beyond which they project.

FIGS. 5 through 8 show elongated bristle heads 14 which are driven linearly in the direction of their longitudinal axes, as indicated with double arrow 15. This linear motion can be overlapped with additional oscillating pivoting motion in accordance with double arrow 16, transverse to the longitudinal axis. A wider bristle stock 17 is disposed on the bristle body 14 beyond which a group of bristles 18 or bundles project whose ends lie along strip-like enveloping surfaces 7. The border edges 8, 9 formed by the bristles of the enveloping surface leading in the direction of motion are formed at an angle with respect to the direction of motion 15, wherein the angle is different in the advancing and returning directions. In the embodiment in accordance with FIGS. 5 and 6, the enveloping surfaces 7 are arrow-shaped and are displaced with respect to the longitudinal axis of the brush head 14.

In the embodiment in accordance with FIGS. 7 and 8, the ends of the bristles projecting beyond the wide surface bristle stock 17 are disposed in a zigzag shaped strip-like enveloping surface 7.

What is claimed is:

1. A brush head, the brush head structured to cooperate with means for driving the head in at least one direction of motion, the brush head comprising:
a first group of bristles attached to the brush head at a bristle mounting surface to extend above said bristle mounting surface for forming an even field of bristles;
a second group of bristles attached to the brush head at said bristle mounting surface, said second group of bristles embedded in said first group of bristles and extending beyond said first group of bristles to form at least one bristle envelope protruding beyond said even field of bristles, said bristle envelope having one of a striped and spotted shape, said bristle envelope defining at least one first bordering edge, leading in the direction of motion of the brush head, wherein each of said at least one first bordering edge extends at a first angle or at first angles relative to the direction of motion, wherein said first angle or each of said first angles differ from 90°.

2. The brush head of claim 1, wherein said bristle envelope defines at least one second bordering edge trailing in the direction of motion of the brush head, wherein said at least one second bordering edge is substantially parallel to an associated first bordering edge.

3. The brush head of claim 1, wherein said bristle envelope defines at least one second bordering edge trailing in the direction of the motion of the brush head, wherein said at least one second bordering edge is substantially non-parallel to an associated first bordering edge.

4. The brush head of claim 1, wherein the brush head is driven in a circular manner about an axis of rotation and said first bordering edge lies on a curve whose radius of curvature differs from a radius of the brush head.

5. The brush head of claim 4, wherein said first bordering edge lies along a spiral.

6. The brush head of claim 5, wherein said spiral has a middle point lying in said axis of rotation.

7. The brush head of claim 5, wherein said spiral has a middle point which is eccentric with respect to said axis of rotation.

8. The brush head of claim 4, wherein said first bordering edge lies along an S-shaped curve whose cusp point is one of on and proximate to said axis of rotation.

9. The brush head of claim 8, further comprising a plurality of strip-like bristle envelopes having S-shaped curves and a common middle point at cusp points of said S-shaped curves.

10. The brush head of claim 1, further comprising a plurality of bristle envelopes, the brush head being driven about an axis of rotation, wherein surface centers of gravity of said bristle envelopes are disposed outside said axis of rotation.

11. The brush head of claim 10, wherein said bristles envelopes lie entirely outside said axis of rotation.

12. The brush head of claim 1, wherein the brush head is elongated along a longitudinal axis and is structured to be driven by a linear drive acting at least along said longitudinal axis, wherein said bristle envelope extends in a zigzagged or waved manner in said longitudinal direction.

13. The brush head of claim 1, wherein the brush head is elongated along a longitudinal axis and is structured to be driven by a linear drive acting at least along said longitudinal axis, and further comprising a plurality of bristle envelopes having surface centers of gravity outside of said longitudinal axis.

14. The brush head of claim 1, wherein said brush head is elongated along a longitudinal axis and is structured to be driven by a linear drive acting along said longitudinal axis, and further comprising a plurality of stripe-shaped bristle envelopes, arrowed in a longitudinal direction, said bristle envelopes disposed at both sides of said longitudinal axis in a staggered fashion.

* * * * *

UNITED STATES PATENT AND TRADEMARK OFFICE
CERTIFICATE OF CORRECTION

PATENT NO.     : 6,421,867 B1
DATED          : July 24, 2002
INVENTOR(S)    : Weihrauch, Georg It is certified that error appears in the above-identified patent and that said Letters Patent is hereby corrected as shown below:

<u>Column 1,</u>
Line 62, please insert as a paragraph following -- It is the underlying purpose of the invention to propose a brush, in particular for electric toothbrushes, which facilitates a plurality of different operating directions for the bristles even in the event of a simple motional drive for the brush head. --.

Signed and Sealed this

Nineteenth Day of November, 2002

*Attest:*

*Attesting Officer*

JAMES E. ROGAN
*Director of the United States Patent and Trademark Office*